(12) United States Patent
Lam

(10) Patent No.: US 8,940,013 B2
(45) Date of Patent: *Jan. 27, 2015

(54) HUMAN SKIN TREATMENT ARRANGEMENT

(76) Inventor: Peter Ar-Fu Lam, Torrance, CA (US)

(*) Notice: Subject to any disclaimer, the term of this patent is extended or adjusted under 35 U.S.C. 154(b) by 156 days.

This patent is subject to a terminal disclaimer.

(21) Appl. No.: 13/573,388

(22) Filed: Sep. 13, 2012

(65) Prior Publication Data
US 2013/0018332 A1 Jan. 17, 2013

Related U.S. Application Data

(63) Continuation-in-part of application No. 12/004,623, filed on Dec. 24, 2007.

(51) Int. Cl.
A61F 5/08 (2006.01)
A61B 17/20 (2006.01)
A61K 8/02 (2006.01)
A45D 44/22 (2006.01)
A61Q 19/08 (2006.01)

(52) U.S. Cl.
CPC .............. A61K 8/0208 (2013.01); A45D 44/22 (2013.01); A61K 8/0212 (2013.01); A61Q 19/08 (2013.01)
USPC .......................................... 606/204.15; 604/46

(58) Field of Classification Search
USPC ...................................................... 606/204.35
See application file for complete search history.

(56) References Cited

U.S. PATENT DOCUMENTS

2002/0111600 A1* 8/2002 Cormier et al. ............... 604/506

* cited by examiner

Primary Examiner — Tuan V Nguyen

(57) ABSTRACT

A human skin treatment arrangement configured to treat surface conditions of human skin, especially the wrinkle, fine lines or scar appeared on the surface of human face, or for improving absorption efficiency of cosmetic or medical transdermal agent. In a treatment mode, the arrangement is configured for attaching to a portion of human skin such that the area of the human skin under treatment is maintained in a stretched position to enhance the treatment effect. In a further embodiment, the arrangement comprises a wrinkle relief agent, a scar relief agent or a cosmetic or medical transdermal agent to treat the surface of the skin.

20 Claims, 8 Drawing Sheets

HUMAN SKIN TREATMENT ARRANGEMENT

This is a continuation in part application of pending U.S. patent application Ser. No. 12/004,623 filed Dec. 24, 2007. Condition of human skin deteriorates due to several factors, such as exposure to harmful rays, natural aging, body fat, wound, infection or even stress. Wrinkle and fine lines appear when skin condition deteriorates. Different formulae or compositions of skin treatment agents are provided in the market aimed to relief skin wrinkle, reduce scar or other deterioration effects. It is an objective of this invention to provide an improved skin treatment arrangement that helps the skin treatment agents available in the market to achieve better treatment effect. It is also an objective of this invention to provide an improved skin treatment arrangement that helps to relief skin fine lines and wrinkles appears on human face. Another particular objective of this invention is to provide a system arrangement suitable for delivering a transdermal agent through human skin, or for skin treatment arrangement suitable for overnight application. It is a further objective of this invention to provide an easy to operate design that reduces a skin wrinkle line, or to improve efficiency of delivering transdermal agent by stretching the two sides of the portion of skin under treatment.

BACKGROUND OF THE INVENTION

Field of the Invention

This invention relates generally to treatment arrangement provided for improvement of human skin conditions or for delivering an agent through human skin.

SUMMARY OF THE INVENTION

The present invention is directed to a skin treatment arrangement provided to improve skin condition or to improve efficiency of delivering transdermal agent with consistent mechanical stretching force in a desired direction to the region of the skin under treatment. In a first application, the skin treatment arrangement is applicable to help surgical wound to recover and to reduce the amount of scar formed. In a further application, the present invention is provided to supplement skin treatment agent available in the market, so as to provide enhanced treatment effect. More particularly, the present invention is directed to help relieving formation of wrinkle or fine lines appeared on the skin of human face by stretching the two sides of the wrinkle line. In another further application, the present invention is to improve the efficiency of transdermal agent delivery with the support of a miniature skin penetrating device. According to a further research of the invention, an easy to operate design is provided to stretch the skin for extended time by a simple pressing or squeezing motion. The term skin treatment arrangement is defined as a setup of one or more treatment members configured to make physical contact with skin surface so as to improve conditions of the skin, or to improve delivery of transdermal agent.

In a first embodiment, an attachment member is provided to represent the structural member of the treatment arrangement. Attachment member in general is hereby defined as the structural member that is attached to the surface of human skin during treatment. Attaching means are provided at positions A and B, located around the two ends of the attachment member. The attaching means are designed for adhering the attachment member with the skin surface under treatment. Accordingly the generic term attaching means is defined as any design and/or method configured for adhering or securing the attachment member with the surface of human skin. The attaching means located at positions A and B are separated by a first distance D1 apart to provide an initial mode. The positions A and B can be extended or stretched in a treatment mode to provide a distance D2 apart, wherein D2 is longer than D1. Initial mode is defined as the mode of the human skin treatment arrangement before the distance between positions A and B is extended. Initial mode is the default condition of the skin treatment arrangement before it is applied to treat the skin. Treatment mode is defined as the mode of the human skin treatment arrangement after the distance between positions A and B is extended to a longer distance apart than that of the initial mode. In between the positions A and B is a treatment portion to provide treatment for the skin. This is also the area for receiving or applying a treatment agent when it is desirable. Wrinkle treatment agent is defined as any medication suitable for reducing wrinkle line or preventing formation of wrinkle line. Scar treatment agent is defined as any medication suitable for preventing formation of scar. Transdermal agent is defined as any medication designed for absorption through the skin. Treatment portion is defined as a portion of the arrangement configured to accommodate treatment agent for treatment of the skin surface or to accommodate a transdermal agent. Treatment portion may be structured as an integral part of the attachment member, or a part separated from the attachment member. In another embodiment, built-in agent is embedded in the treatment portion during the manufacturing process of the attachment member. Built-in treatment agent in general is defined as the agent that was factory applied to a part of the arrangement before the human skin treatment arrangement is provided to the end user. Examples of typical treatment agents are the agent formulated for reduction of scar, relieving of wrinkle lines, fine lines, agent designed for medical treatment of skin infection, or any other medical or cosmetic agent designed to be absorbed through human skin.

During an application process of the first embodiment, the attachment means located at positions A and B are positioned across the skin treatment area, pressed and adhered to the surface of the skin, so as for the treatment portion to make contact with the skin surface under treatment. The positions A and B are then stretched, or extended to a longer distance D2 apart, where D2 is longer than D1. It is essential for the attachment member to have at least an elastic or flexible portion located in between the positions A and B, so as for the attachment member to be stretched or extended. The longer distance D2 of positions A and B during the treatment mode is maintained by a distance maintenance means. Distance maintenance means is therefore defined as any design and/or method configured for securing the longer distance D2 between the positions A and B during the treatment mode. Usually the distance maintenance means comprises a flexible member, which provides adequate stretch force to maintain the extended distance D2 between positions A and B during the treatment mode. Proper amount of stretch force and the amount of extension of the attachment member during the treatment mode are the variables to be properly determined in the design process of the distance maintenance means in order to provide optimal treatment effect. These variables are particularly important when the skin treatment arrangement is provided to reduce scar during wound recovering. Stretch force is determined by the elastic or flexible force provided by the distance maintenance means. Extension range is determined by the stretch or extension limitation provided by the mechanical design of the distance maintenance means. The term "Extension Ratio" represented by the symbol "R" is defined as the ratio between the D2 distance during the treatment mode and the D1 distance during the initial mode. Accordingly R is defined by the equation R=D2/D1. The ratio R is an important parameter in the design of attachment member, because different values of R are required to treat different kinds of wrinkle lines or scar during the different stages of the treatment process.

There are different ways to securely attach the attachment member with the skin surface. The first method is by adhesive. The adhesive should be carefully formulated to avoid sensitivity reaction, such as rash of the skin. The adhesive should also be composed to endure reasonable skin surface excretion such as oil or sweating, for at least several hours. Accordingly the statement for an "attaching means to be configured for adhering an attachment member to the surface of human skin" is defined by the following two characteristics:

(a) The attaching means should be free from creating adverse reaction to the skin during the specified treatment period; and (b) The attaching means should be able to maintain a reasonable adhesive force between the attachment member and the skin in the stretched treatment mode during the specified treatment period.

For a skin treatment arrangement configured for overnight treatment, the desirable treatment period can be specified to be at least seven hours.

When the skin treatment arrangement is provided to treat wounds, or to reduce scar in surgical operation, the attachment member can be stitched to the surface of the skin under treatment. When stitching process is applied, it is required that the material used to manufacture the attachment member to be suitable for the stitching process.

According to the different embodiments of the invention, different kinds of distance maintenance means are illustrated. In a first embodiment, the distance maintenance means is represented by a single formed spring wire. Both terminal ends of the wire are to be received by two receivers located at the end of the attachment member to provide the stretched treatment mode. In a second preferred embodiment, the distance maintenance means is characterized by two plastic portions protruded towards the sides of the attachment member. Transforming the initial mode into the treatment mode is achieved by squeezing the two protruded portions. In a third preferred embodiment, a single plastic portion protruded outward from the non-treatment surface of the attachment member is provided. Transforming the initial mode into the treatment mode is achieved by pushing or pressing the protruded portion towards the skin surface under treatment. In another further embodiment, multiple distance maintenance means are provided in a row on top of an attachment member to provide a larger treatment area. A further configuration of the distance maintenance means is to provide a hollow region around the central portion of the arrangement for delivering transdermal agent in solid form or in the form of agent container or an agent cartridge.

Several methods to connect the distance maintenance means with the attachment member are disclosed. In a first arrangement, both ends of the distance maintenance means are separated from the attachment member. In a second design, one end of the distance maintenance means is secured to the attachment member by stitching, molding or welding process. In a third design, both ends of the distance maintenance means are secured to the attachment member when it is manufactured.

Different embodiments of the attachment member is characterized by the different shapes and dimensions of the attachment member, so as for it to suit for different application environments. For some typical standard size designs, the dimension of the D2 is usually shorter than one inch. In rare application situations for treatment of large surface area, D2 separation of up to 2 inches is possible. In another preferred embodiment, the attachment member is designed to provide a curved shape, so as for it to fit typical curved wrinkle lines appeared on the human face located on the two sides of the mouth area. In yet another preferred embodiment, the attachment member is provided in the form of a row. The attachment member is cut from the row according to the length of the wound, or scar to be treated. Another attachment member embodiment configured in the shape of a mask is also disclosed to treat wrinkle lines of the whole face, all at one time. The guideline is that the area of service provided by the attachment member should be of customary shape adequate to cover the shape and size of the wrinkle lines, wound or other skin surface under treatment.

According to another application, the arrangement is provided to improve the absorption rate of transdermal agent. A penetrating device having multiple miniature penetrating protrusions is provided to create miniature penetrating openings to a surface of human skin. The skin surface is then stretched and maintained to increase the openings of the miniature penetrations. Transdermal agent is then applied to the treated skin surface. The stretched miniature skin openings helps to improve the absorption rate of the transdermal agent.

During the research of the subject invention it was discovered that variables such as attachment members of different shapes, dimensions, different stretch force and different R factors are required for treatment of different types of wrinkle lines, wounds, or to work with different kinds of transdermal agent delivery devices. In some special applications, the R factor is to be gradually reduced or increased during the whole treatment process to provide the optimal treatment effect. Accordingly different types of skin treatment retail packages are to be provided, each with a collection of attachment members of different characteristics, suitable for a specific treatment objective. In another skin treatment retail package, the different treatment agents are separated from the attachment members so that the user has the flexibility to determine which treatment agent and the amount of dose to be applied. Due to the complexity of selecting the proper application arrangement according to all these variables, it is also important for the skin treatment retail package to provide adequate instruction informing the user how to select the most appropriate attachment member during a particular time of the treatment process. In particular, the skin treatment retail package instruction should also provide information to the user that the positions A and B of said attachment member should be applied across the wrinkle line or fine line of the human skin to be treated; and that the direction of positions A and B of said attachment member should be properly aligned to be perpendicular to the wrinkle line or fine lines under treatment. These information are required for the user to achieve optimal skin treatment effects.

The novel features of the invention are set forth with particularity in the appended claims. The invention will best be understood from the following description, when read in conjunction with the accompanying drawings.

DESCRIPTION OF THE DRAWINGS

FIG. 5b is the sectional view of the scar 507 of FIG. 5a;

FIG. 12a illustrates an alternate embodiment of the treatment arrangement in the form of a mask; and FIG. 12b illustrated an embodiment of the distance maintenance means for use with the mask of FIG. 12a.

DETAILED DESCRIPTION

Figure 1A:
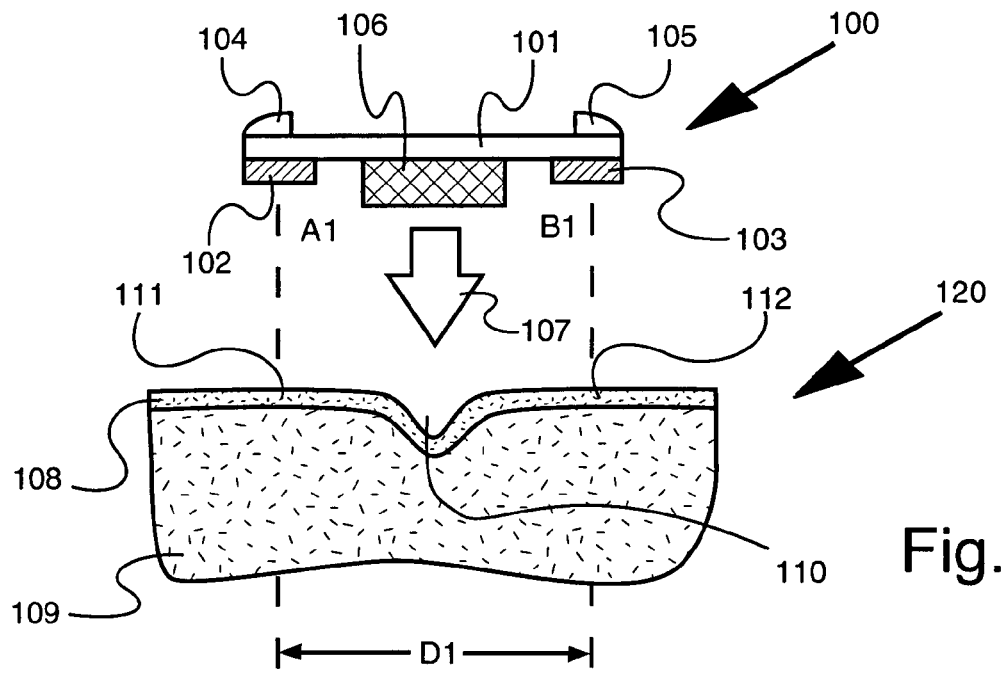
FIG. 1a is the sectional view of a first embodiment of treatment arrangement before it is applicable to treat wrinkle of human skin.
Figure 1B:
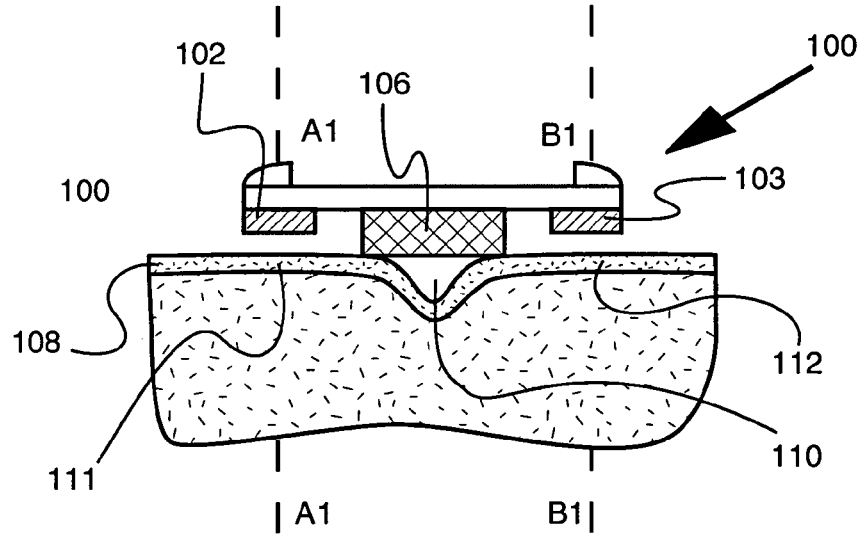
FIG. 1b is the further sectional view of the arrangement of FIG. 1a when the treatment arrangement is applicable to treat wrinkle of human skin.
Figure 1C:
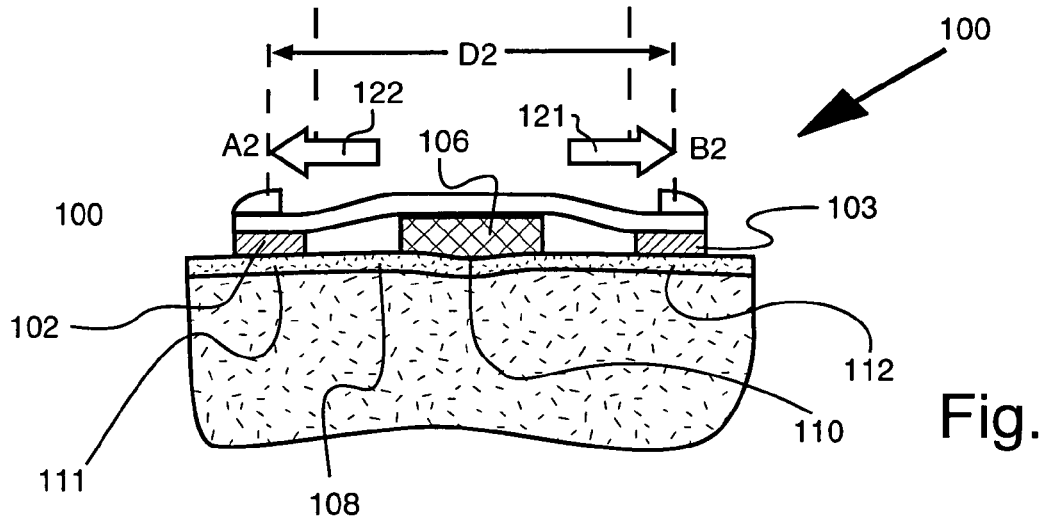
FIG. 1c is the sectional view of FIG. 1b wherein the treatment member is stretched to define a treatment mode.

Attention is initially directed to FIG. 1a, which is the sectional view of a first embodiment 100 of the treatment arrangement. The application example is to treat wrinkle of human skin 108. The treatment arrangement 100 comprises an attachment member 101. At the two ends of the single piece attachment member 101 are the attaching means 102 and 103 locating at positions A1 and B1. In between positions A1 and B1 is a treatment portion 106. The treatment portion 106 may be configured to be permanently or irremovably connected to said attachment member 101. On the other side of the attachment member 101 are the first two distance maintenance members 104 and 105. The distance between A1 and B1 is represented by a distance D1 apart. The view 120 illustrates a sectional view of a portion of human skin under treatment. The human skin section illustrated a skin layer 108 and the tissue layer 109. In between the surfaces 111, 112 of the skin layer 108 is a recess region 110. This recess region represents the sectional view of a wrinkle line appeared on the surface of the skin. In a treatment process, a wrinkle treatment agent that helps to relief the wrinkle 110 is pre-applied to the surface of the wrinkle line 110. Alternately the treatment agent is pre-applied to the treatment portion 106. The attachment member 101 is then applied in the direction 107 towards the surface of the wrinkle line 110. FIG. 1b illustrates the condition when the treatment portion 106 is in touch with the wrinkle line 110. In a typical arrangement, the attaching means 102 and 103 are provided with adhesive suitable for adhering the attachment member 101 with the surface of human skin. Design of the attaching means such as selection of adhesive material is important. Since the adhesion is required to maintain the D2 distance as well as the stretch force of the skin during the long treatment period, the design and adhesive material selected should not cause adverse side effect, such as rash to the skin of the user. The design is also required to withstand reasonable change of skin conditions, especially those caused by reasonable excretion of skin oils or sweating. It should be noted that the attaching means 102 and 103 should be located on the two sides of the wrinkle line 110, so as for the treatment portion 106 to positioned on top of the wrinkle line 110. The treatment portion is preferably to comprise an elastic and absorbent material such as medical grade spongy material so as to absorb the treatment agent; and also to maintain the pressure of treatment agent towards the wrinkle portion 110 of the skin during the treatment process. A spongy material provided as the treatment portion is optional when the treatment agent is applied directly to the surface of the skin prior to treatment. FIG. 1c illustrates the effect that the spongy treatment portion 106 is compressed in between the attachment member 101 and the skin surface 108, after the attachment means 102, 103 are adhered with the skin surface. The attachment member 101 is then stretched towards the directions 121, 122 such that the skin surfaces located on the two sides of the wrinkle line 110 is pulled apart towards the positions A2 and B2. The distance D2 between the positions A2 and B2 during the treatment mode is longer that the distance D1 of the initial mode. This process allows the depth of the wrinkle line to be reduces and for the inner surface of the wrinkle line to make better contact with the treatment agent. The user is recommended to leave the treatment overnight in the stretched treatment mode. The invented treatment arrangement of FIG. 1c provides significant better treatment result to relief wrinkle or fine lines than the traditional arrangement of applying just the treatment agent alone.

Figure 2:
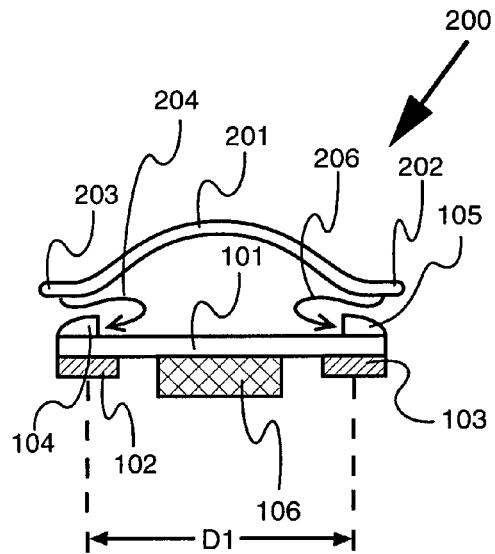
FIG. 2 is the sectional view of an embodiment having a distance maintenance means provided for maintaining the stretched distance of a treatment member.
Figure 3:
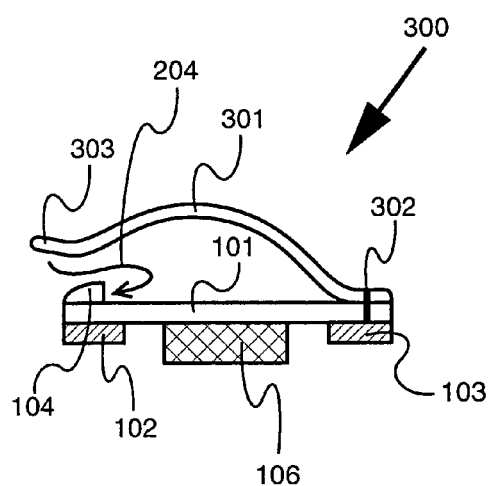
FIG. 3 illustrates an alternate embodiment having a different distance maintenance means.

FIG. 2 illustrates a first embodiment of distance maintenance means to keep the longer distance D2 during the treatment mode. A third distance maintenance member 201 in the shape of a curved spring wire is provided to engage with the first two distance maintenance members 104 and 105. The three members 201, 104 and 105 formed the distance maintenance means of the subject embodiment. The terminal ends 203, 202 of the spring wire 201 are configured to engage with the members 104, 105 respectively. The spring force of the wire 201 provides the force to pull the positions A1, B1 of the attachment member 101 apart. It should be noted that the attachment member 101 should provide at least one elastic region in between the positions A1 and B1 so as for the attachment member to be extended. The extension force is determined by the material and geometry of the spring wire 201. The range of extension is a variable determined by the extension force of the spring wire, the elasticity of the attachment member and that of the skin. FIG. 3 illustrated an alternate embodiment having the terminal end 302 fix with the end of the attachment member 101. This can be achieved by molding, glue, sonic welding or stitch processes. An alternate design is to provide molded plastic material instead of metal wire for the third distance maintenance member. FIG. 3 demonstrated a three layers assembly having a first layer of distance maintenance means 104, 301, a layer of treatment portion 106 and a layer of attachment member 101. All these different embodiments and any other designs capable to accomplish similar results are to be encompassed by the definition of distance maintenance means defined herein.

Figure 4A:
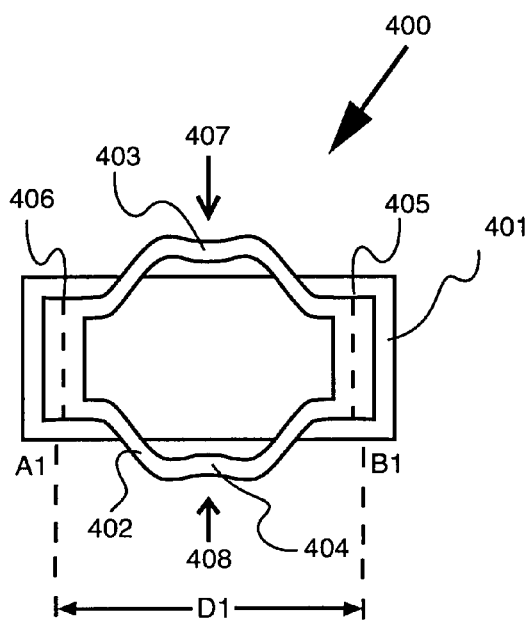
FIG. 4a is the top view of another embodiment having an alternate distance maintenance means.
Figure 4B:
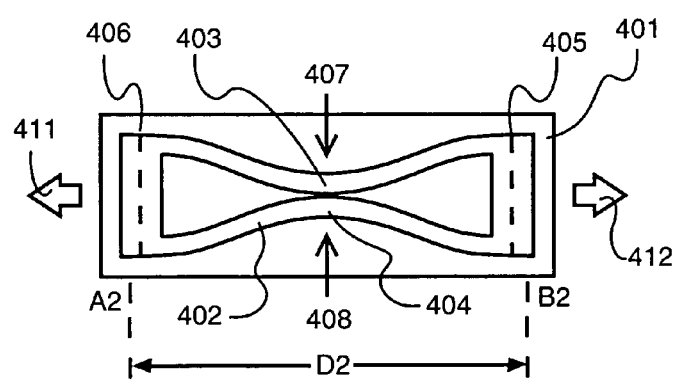
FIG. 4b illustrates the embodiment of FIG. 4a configured to provide the treatment mode
Figure 9A:
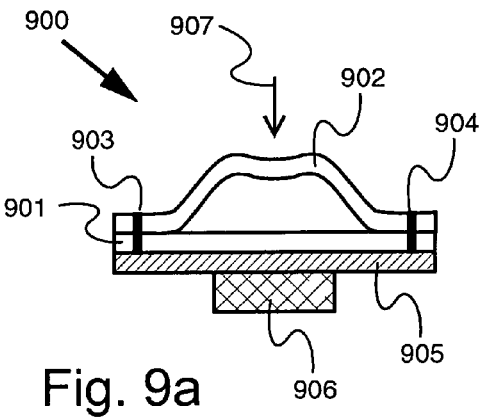
FIG. 9a is the sectional view of an alternate embodiment of treatment arrangement.
Figure 9B:
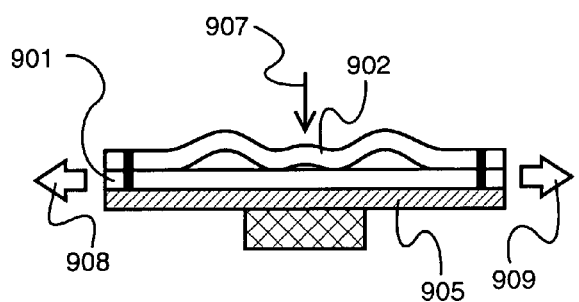
FIG. 9b illustrates the embodiment of FIG. 9a in the treatment mode.

In another preferred embodiment illustrated in FIG. 4a and FIG. 4b, the design of the distance maintenance means is configured to provide a predetermined extension distance D2. The distance maintenance means 402 is preferred to be manufactured with injection molded flexible plastic materials. The two ends 405, 406 of the distance maintenance means 402 is fix to the attachment member 401 by any suitable design such as stitches or sonic welding. The distance maintenance means 402 comprises two protruded side portions 403 and 404 that characterized the initial mode. After the embodiment of FIG. 4a is applied to the skin area under treatment, the protruded side portions 403 and 404 are squeezed to a situation as shown in FIG. 4b. The squeeze motion extends the length of the distance maintenance means in the directions 411 and 412. Accordingly the positions A1 and B1 of the attachment member 401 is extended to the positions A2 and B2, which defines the stretched distance D2 for the treatment mode. When the initial mode 400 of FIG. 4a is transformed into the treatment mode of FIG. 4b, the maximum distance D2 is limited to point when the side portions 403, 404 touch each other. The advantage offered by this design is that the amount of extension from D1 to D2 is predictable. This extension distance can then be fined tuned and perfectly controlled in the design stage to provide the optimal treatment effect. According to the research of the invention, a term "Extension Ratio" is formed. This ratio is represented by the symbol R, as defined by the equation $R=D2/D1$. For simplicity, the extension ratio is termed as the R ratio hereunder. Clinical study is required to determine the best value of R ratio for different relief applications as well as to treat different degree of wrinkle. According to the research result of this invention, a treatment arrangement applying a higher value of R is provided to treat severe wrinkle lines on the face. After a first stage treatment for around one week is completed, the treatment is switched to apply attachment members of lower R ration. The R ratio of attachment member can be gradually reduced to a much smaller number when the wrinkle condition significantly improves. Attention is now directed to FIG. 9a, which illustrated another embodiment with predetermined R ratio. As compared with two protruded side portions, the distance maintenance means comprises only one protruded portion 902. Extension of the attachment member 901 is provided by pushing or pressing the protruded portion 902 from the direction 907. FIG. 9b illustrated the side view of the embodiment 900 in the treatment mode. The R ratio is determined by the geometry of the protruded portion 902.

Figure 5A:
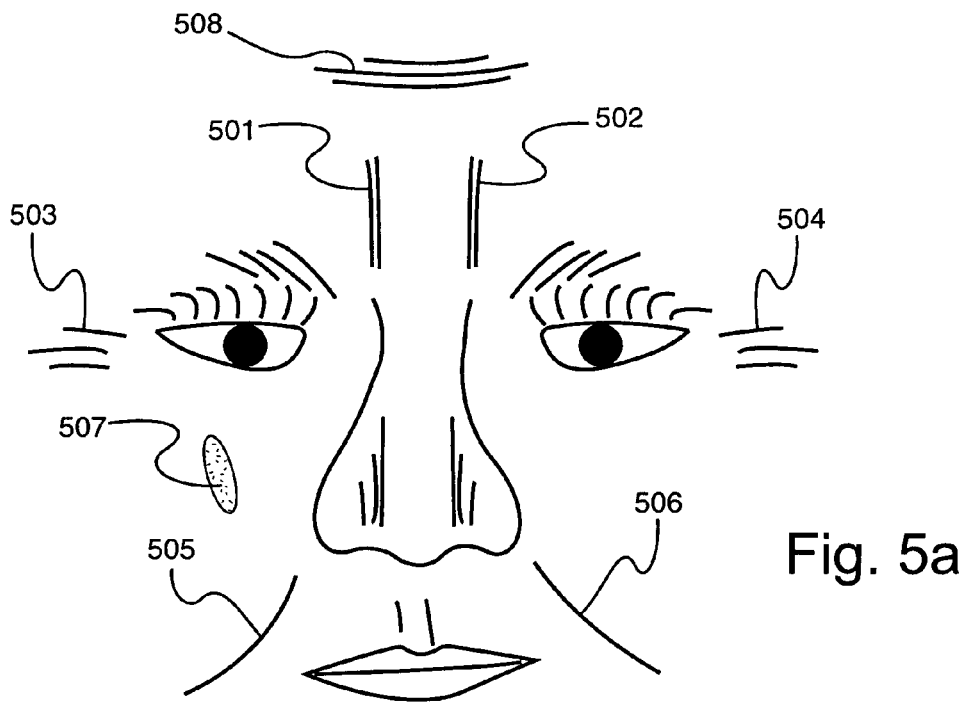
FIG. 5a illustrates typical scar, wrinkle and fines lines located on a human face.
Figure 5B:
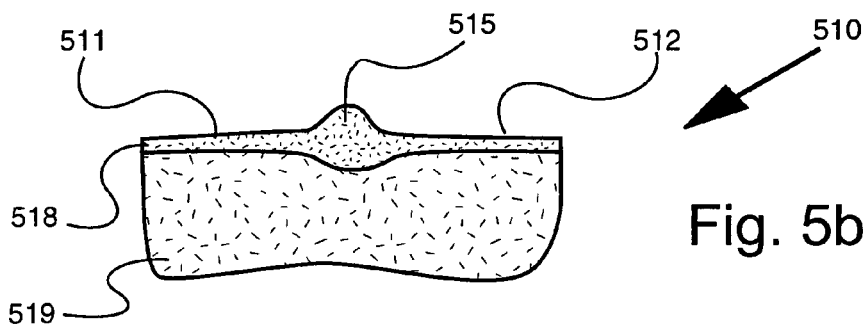

FIG. 5a illustrates typical wrinkle and fines lines appeared on aged face skin. A scar 507 resulted from a wound is also illustrated. The most common wrinkle lines are the horizontal wrinkle lines 508 located on the forehead area, the vertical wrinkle lines 501, 502 located above the nose and between the eyebrows, and the curved lines 505, 506 located on both sides of the mouth. Fine lines 503 and 504 may also be found next to the eyes as illustrated. Because wrinkle lines are of different shapes and lengths, a single fixed size attachment member design is not efficient to service their different needs. Accordingly attachments members of different shapes and extension characteristics are recommended for a skin treatment retail package to treat wrinkle lines of different shapes. FIG. 5b illustrates the sectional view of the scar 507. The scar is formed by thicker skin tissue 515 grown on the skin surface 511, 512 after a wound was cured. The invention research indicated that it is desirable to combine the invented skin treatment arrangement with scar reduction treatment agent to reduce the amount of scar formed during the recovery period of the wound. According to the research study of this invention, the proper time to apply the skin treatment arrangement is around three days to one week after the wound is stitched, depends on the dimension of the wound. In contrast to the treatment of wrinkle lines, attachment member of lower R ratio is first applied to new stitched wounds. The R ratio is gradually increased when the wound cures. Since the initiation to provide attachment members of different R ratios was established, embodiments to provide attachment members of different R ratios were provided, and the importance of providing different R ratios during a treatment process was discovered, the next step is to provide attachment members of different R ratios in a retail treatment package. Properly configuring the content of a skin treatment retail package is an important part of this invention. Skin treatment retail package is defined as a collection of components or members suitable for achieving at least a specific treatment objective and the collection of components or members are packaged together suitable for retail purpose, through retail channels such as for direct to customer retail sales or for retail point of sale. In a first typical skin treatment retail package arrangement, the treatment agent is provided in a container separated from the attachment member, so that the user is free to apply the treatment agent on the surface of skin or the treatment portion before the attachment is applied to the skin. With this design, the user has the control to adjust the amount of treatment agent for each treatment process. In a second typical skin treatment retail package arrangement, an assortment of different shape/size attachment members are provided for treating wrinkle lines of different shapes and sizes. In another embodiment of skin treatment retail package arrangement, attachment members of different R ratios are provided.

Figure 6:
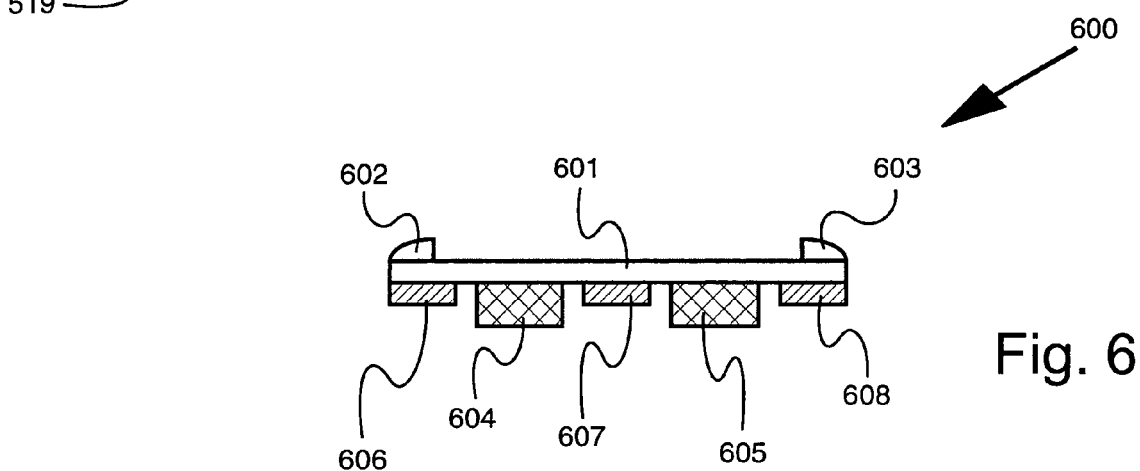
FIG. 6 illustrates the section view of an alternate embodiment having multiple treatment members.
Figure 7:
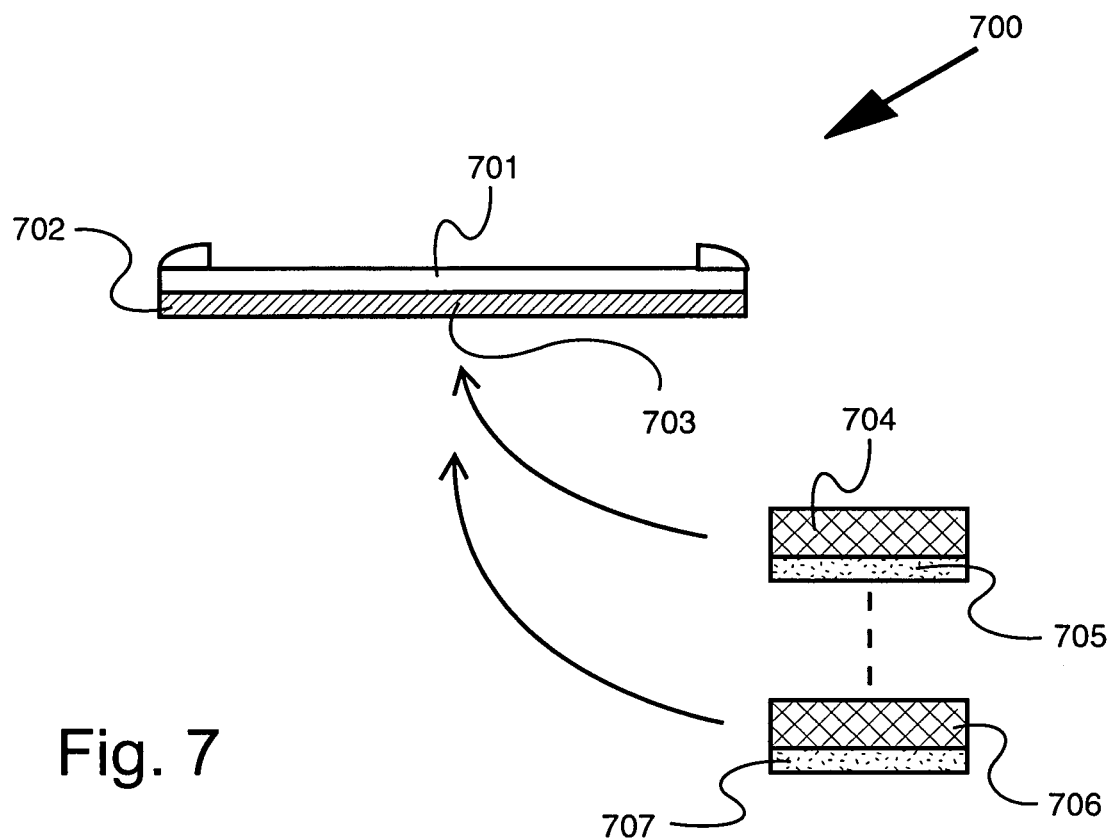
FIG. 7 is an alternate embodiment having different types of treatment member separated from the treatment member.
Figure 8:
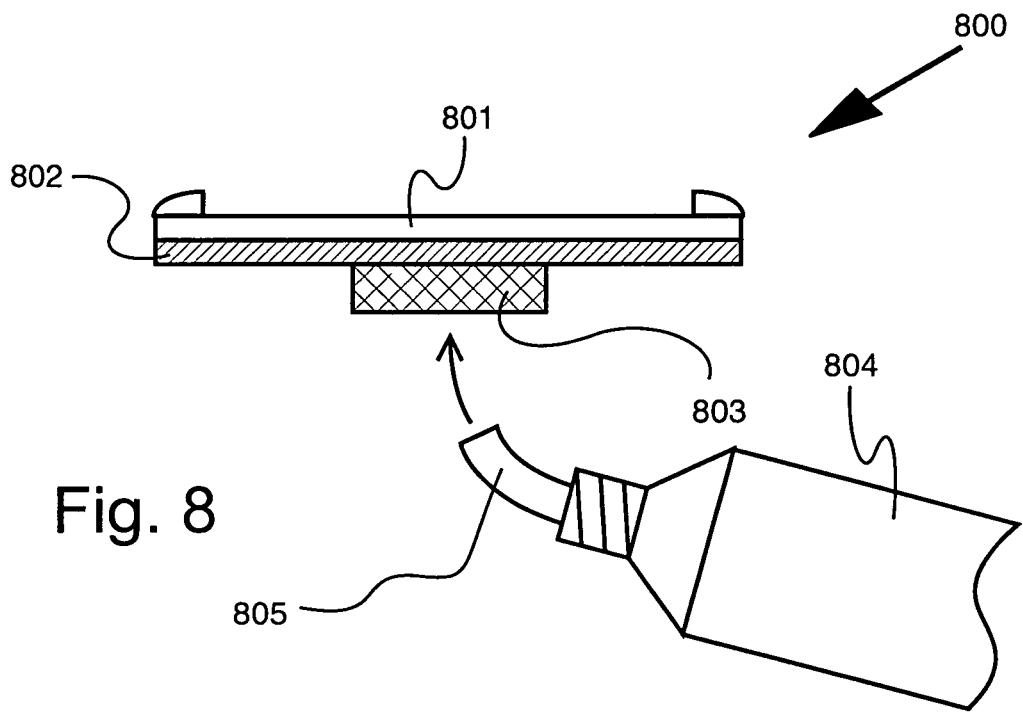
FIG. 8 illustrates a retail treatment package having a separated tube of treatment agent.

Attention is now drawn to FIG. 6, which illustrates an alternate embodiment having multiple treatment portions 604 and 605. In this design three attaching means 606, 607 and 608 are provided for better adhesion effect. This embodiment is an example of specialty attachment member design, particularly suitable for treatment of the wrinkle lines 501 and 502 illustrated in FIG. 5a. FIG. 7 illustrated another alternate embodiment having a generic attachment member 701. Beneath the attachment member 701 is a layer of attaching means 702. Treatment portions 704, 706 are provided to supplement the treatment arrangement. Built-in treatment agent 705, 707 may be provided to the treatment portions 704, 706. Alternately, the user may elect to apply treatment agent, such as those provided in the tube 804 to the skin surface directly or to the contact surface of the treatment portion 803 as illustrated in FIG. 8. According to a first application of the design, treatment portion 803 with built in treatment agent, separated from the attachment member 801, is first applied onto the treatment area of the skin surface. The attachment member 801 is then applied to cover the treatment portion. The advantage of this design enables a user to accurately place the treatment portion on top of the spot to be treated. In a second application of the design, treatment portion 704 and/or 705 are applied to adhere with the attachment member 701 first, the assembly is then applied to the treatment area as previously described. The first advantage of this embodiment is that multiple treatment portions can be applied to the attachment body 701 to enlarge the treatment area. The second advantage is that treatment portion 705, 706 with different treatment characteristics, such as different composition or different dose of treatment agent may be provided in a skin treatment retail package allowing the user to determine which type of treatment portion, and which application process is most appropriate for the treatment process.

FIG. 9a and FIG. 9b illustrate an alternate embodiment, which provides simpler operation process than the other embodiments previously discussed. This embodiment also provides treatment arrangement with predetermined R ratio. Instead of providing segments of attaching means, a layer of attaching means 905 is provided. The treatment portion 906 is a very soft spongy material such that the pushing motion in the direction 907 will securely adhere the attaching means 905 with the skin surface before stretching motion of FIG. 9b is started. The process to transform the initial mode of FIG. 9a into the treatment mode of FIG. 9b is achieved by pushing the protruded distance maintenance means 902 in the direction 907.

Figure 10A:
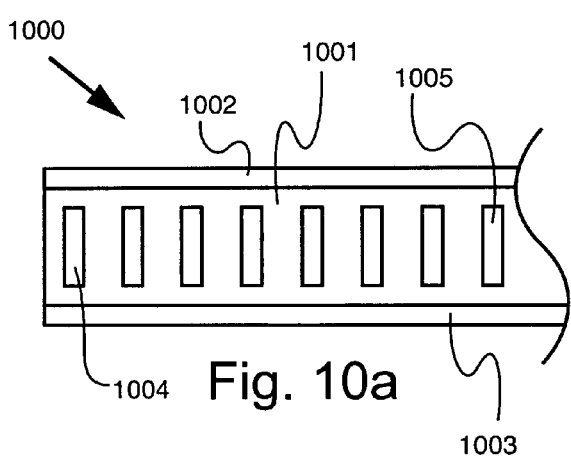
FIG. 10a is the top view of an alternate embodiment having multiple distance maintenance means.
Figure 10B:
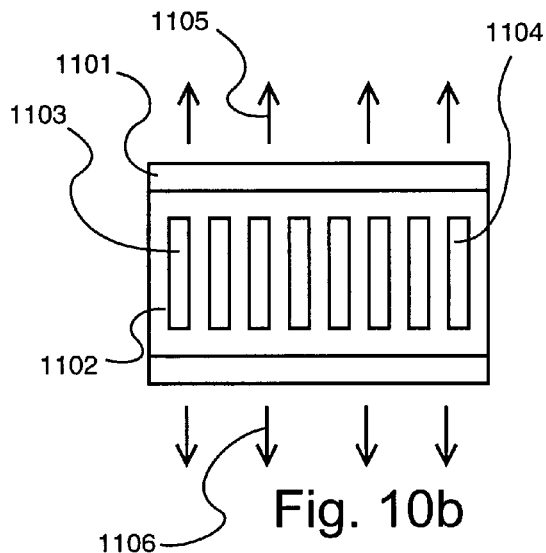
FIG. 10b illustrates the embodiment of FIG. 10a in the stretched treatment mode.
Figure 11:
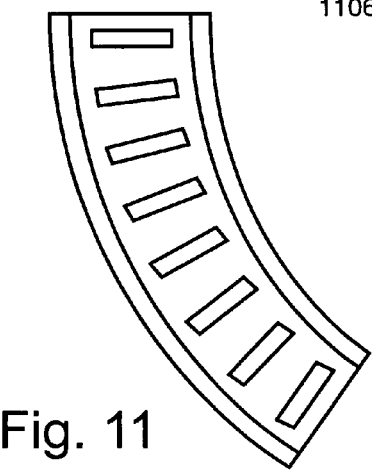
FIG. 11 is an alternate embodiment of FIG. 10a to provide a curved treatment arrangement.

FIG. 10a shows the top view of an alternate embodiment that provides a long strip of attachment member 1001. This design is to service skin treatment of extended size, such as long scars. The two edges 1002 and 1003 are provided with attaching means on the skin contact side. On top of the attachment member 1001 are rows of distance maintenance means 1004 to 1005, each is similar in design to the protruded member 902 of FIG. 9a. The treatment arrangement may be supplied in the form of a row. The appropriate length of attachment member is cut as need according to the length of the wound or scar to be treated. The segment of treatment member is then aligned in parallel with the scar such that the attaching means are positioned on the two sides of the scar. After pressing the attaching means to securely adhered with the skin surface, each distance maintenance means 1004 to 1005 is pushed or pressed so that the width of the attachment member extends in the direction 1105 and 1106 as shown in FIG. 10b to form the treatment mode. FIG. 11 illustrated another embodiment provided with a attachment member having a curved foot print. This design can be specifically dimensioned to treat a typical long curve wrinkle such as the lines 505 and 506 of FIG. 5a. Alternately this embodiment can be alternately dimensioned to treat predetermined surgical wound or scar such as the surgical wound required to deliver a baby. In surgical application, it is possible for the surgeon to stitch the treatment arrangement of FIG. 10a and FIG. 11 onto the wound so as to provide a long lasting adhesive force between the treatment member and the skin under treatment.

Figures 12A, 12B:
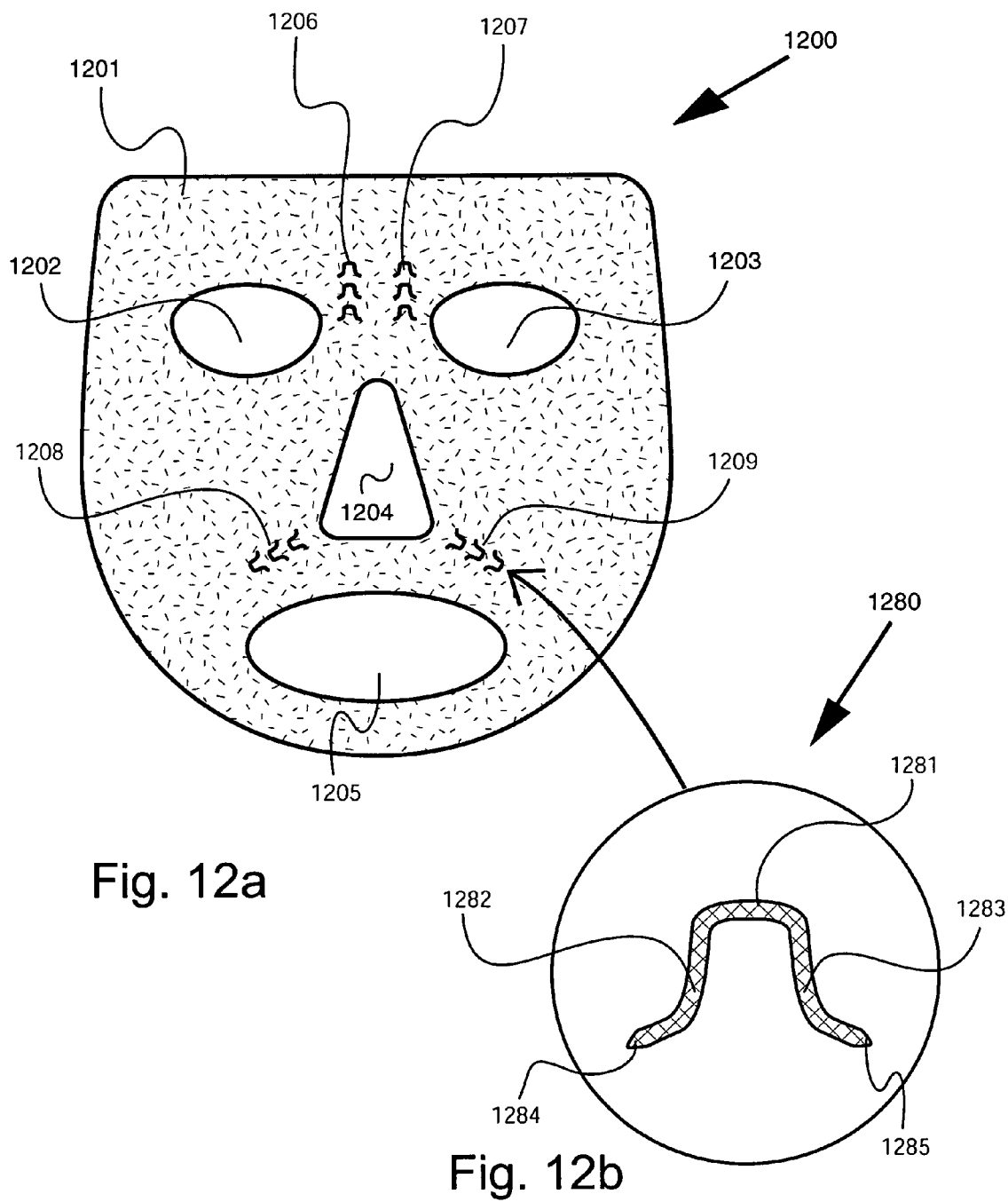

FIG. 12a illustrated another embodiment suitable to treat multiple wrinkle lines of a face. The attachment member is provided in the shape of a mask. Opening 1202, 1203, 1204 and 1205 are provided for the positions of the eyes, nose and the mouth. Beneath the mask is a layer of attaching means, which is also compounded to provide the effect of treatment agent. This layer is configured to provide both the adhesive and treatment purposes. An improved version of the mask is preferred to be transparent or semi transparent, such that the wrinkle lines are visible after the mask is adhered to the surface of the skin. Rows of distance maintenance means 1206, 1207, 1208 and 1209 are applied to extend the region of attachment member on the two sides of the wrinkle lines under treatment. FIG. 12b illustrates an embodiment of the distance maintenance means suitable for the mask shape of attachment member shown in FIG. 12a. The two sides 1282 and 1283 are squeezed before applied to the mask, along the wrinkle line. When the squeeze motion is released, the skin surface across the wrinkle line is extended to provide the treatment mode. Because each distance maintenance member comprises two sharp points to work with the mask, two steps were developed during the research of this embodiment to provide a safe design. The first step is the addition of an elastic protective layer in between the top layer of attachment member and the bottom layer of attaching means. The second step is to increase the thickness of the attachment member to over 1 mm. It should also be noted that the embodiment of FIG. 12b is exemplary, any design meeting the definition of distance maintenance means are to be encompassed in the scope of the subject claims.

Figure 13:
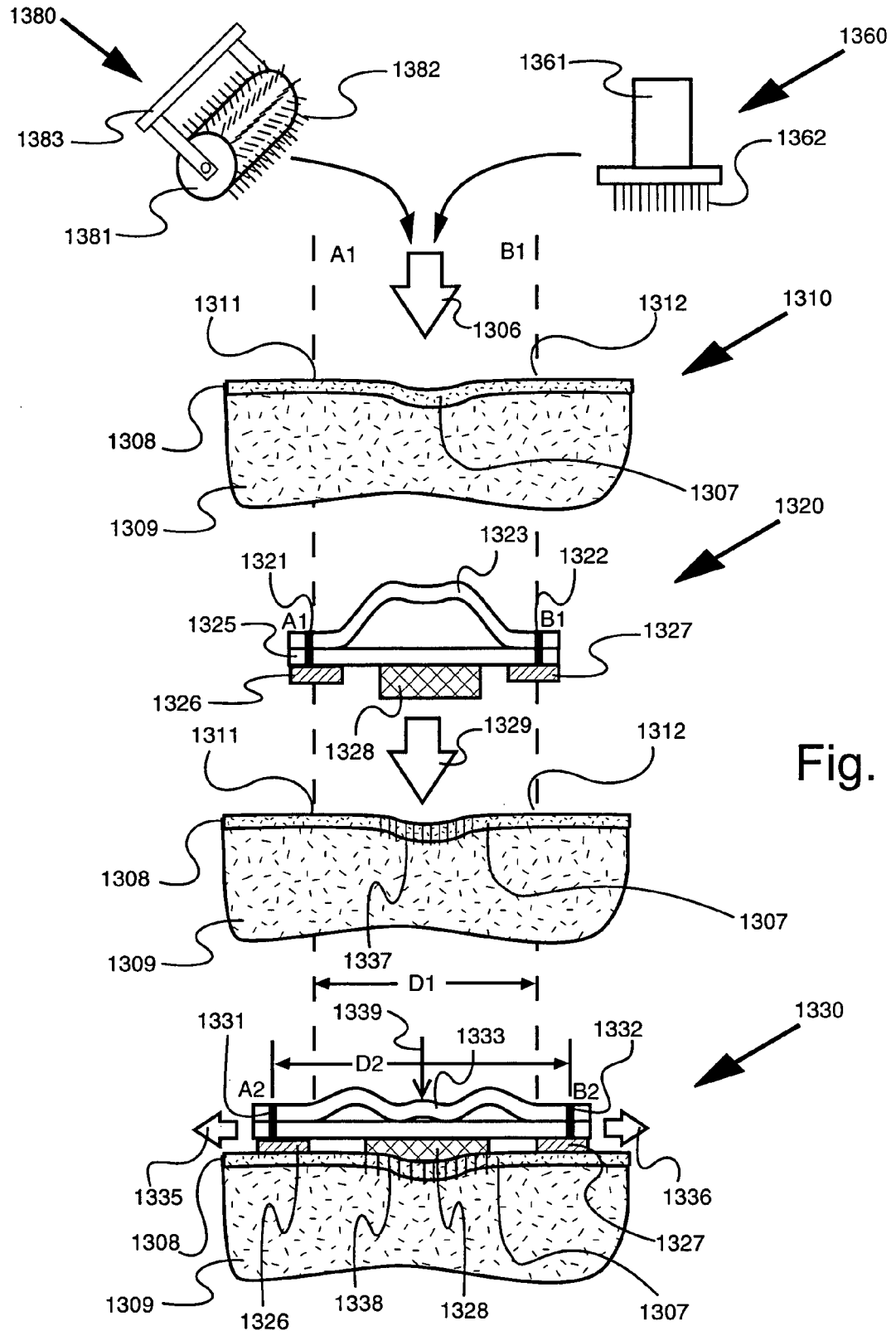
FIG. 13 illustrates the arrangement for delivery of transdermal agent.

Attention is now directed to FIG. 13 describing an alternate application of the subject invention for improving transdermal agent absorption. It is highly recommended to provide in the treatment arrangement package a disinfectant wipe such as alcohol wipe for cleaning and disinfecting the skin surface before applying the transdermal agent delivery process. Device 1380 represents a penetrating device having multiple miniature penetrating protrusions 1382, such as pins, provided for creating miniature penetrating openings to a surface of human skin 1308. 1383 is the handle of the penetrating device 1380, provided for rolling the drum 1381 on the surface of the skin surface under treatment, so as to create miniature penetrating openings 1337 onto the skin surface 1308. Alternate penetrating device 1360 provides multiple miniature penetrating protrusions, or pins 1362 at the bottom of a stamp shape structure 1361. Operation of the device is achieved by simply stamping the pins 1362 in the direction 1306 onto the skin surface 1308 under treatment. After miniature penetrating openings 1337 are created on the skin, an attachment member 1325 having attachment means 1326, 1327 separated at a distance D1 apart is applied in the direction 1329. The attachment member 1325 is made of elastic material that allows the separation D1 to be extended. When the portion 1323 is pressed towards the direction of the skin surface, the attaching means 1326, 1327 are forced to move to the directions 1335, 1336 for an extended separation D2 away. Extension of the two attaching means 1326, 1327 stretch the miniature penetrating openings 1337 into wider openings 1338. The portion 1323 is deformed into the shape 1333 to maintain the extended separation D2. Human body absorption efficiency of the agent located in treatment portion 1328 is significantly improved by the extended miniature penetrating openings created by the treatment arrangement. It should be noted that the components or members 1323, 1325, 1326, 1327 are preferred to be automatically assembled into a single treatment assembly in the factory. 1320 of FIG. 13 demonstrated a three layers assembly having a first layer of distance maintenance means 1323, a layer of treatment portion 1328 and a layer of attachment member 1325. Depends on the nature of the treatment agent, treatment assemblies or attachment members of different shapes, dimensions, extension ratio R, different stretch forces may be packaged together in a retail packaging for the convenience of the user, such as for treating different positions of a human body or different conditions of the skin under treatment.

The bottom view of the penetrating device 1360 is represented by the illustration 1400. Multiple miniature penetrating protrusions in the form of miniature blades 1402 are provided at the bottom 1401 of the stamp. Illustration 1410 represents the skin surface under treatment. 1418 are the miniature penetrating openings of the skin created by the miniature blades 1402 after step A, stamping of the penetrating device 1361, or 1400 onto the surface of the skin under treatment. 1403 represents the footprint of the multiple miniature penetrating blades 1402, which will create a corresponding footprint 1411 of the miniature penetrating openings 1418 created. In the next step B, the arrangement 1420 is then applied on top of the stamped skin surface. The adhesive attaching means 1421, 1422 located beneath the single piece attachment member 1423 securely adhere the frame 1423 to the surface of the skin under treatment. The central portion 1429 is a hollow region configured to receive treatment agent to be applied at a later time. When the flexible portions are pressed towards the center of the frame 1423, the attaching means are forced to extended towards the directions 1431, 1432 as shown in step C. The central hollow area 1429 is extended to provide an extended hollow area 1439. The extension is limited by the flexible portions 1427, 1428, when they are fully extended to the shape of 1437, 1438. Dimensions of the flexible portions 1427, 1428 are critical for controlling the amount of extension for providing a exact final extended shape of the hollow opening 1439. Step C transforming the arrangement 1420 into the shape of 1430 is reflected by the step C1 for transforming the footprint 1411 of the skin surface 1410 into the extended foot print 1461, whereas the distance D1 is extended to a controlled distance D2. The openings of the miniature penetrating openings 1418 are enlarged to the shape 1468 as shown. In the next step D, agent 1485 in the form of ointment stored in a tube 1481 is applied to the hollow region 1439. The applied ointment is then covered by the pad 1472 of footprint matching the controlled dimensions of the hollow region 1439. In step G, finally an adhesive bandage or tape 1491 is applied to cover the arrangement and to secure/maintain the extended shape of the treatment mode of the arrangement. Alternately in step E, an agent in solid form of dimension matching the extended hollow region 1439 is inserted into the hollow region. The agent 1482 in solid form or soft wax form is designed to be slowly dissolvable or absorbable once it is making contact with human skin, for lasting agent delivery effect. In an alternate embodiment, the agent 1488 is provided in a container cartridge 1483. In step F, the agent containing cartridge of dimensions matching the hollow opening 1439 is inserted into the hollow region, allowing the agent to make contact with the skin surface created with miniature penetrating openings. The triangular shaped ridges 1487 allows the agent container or cartridge to securely stay with the frame 1423 once it is inserted. Similarly, an adhesive bandage or tape 1491 is provided to cover and secure the extended arrangement after the wax form agent of 1482 or the agent cartridge 1488 are applied.

Figure 14:
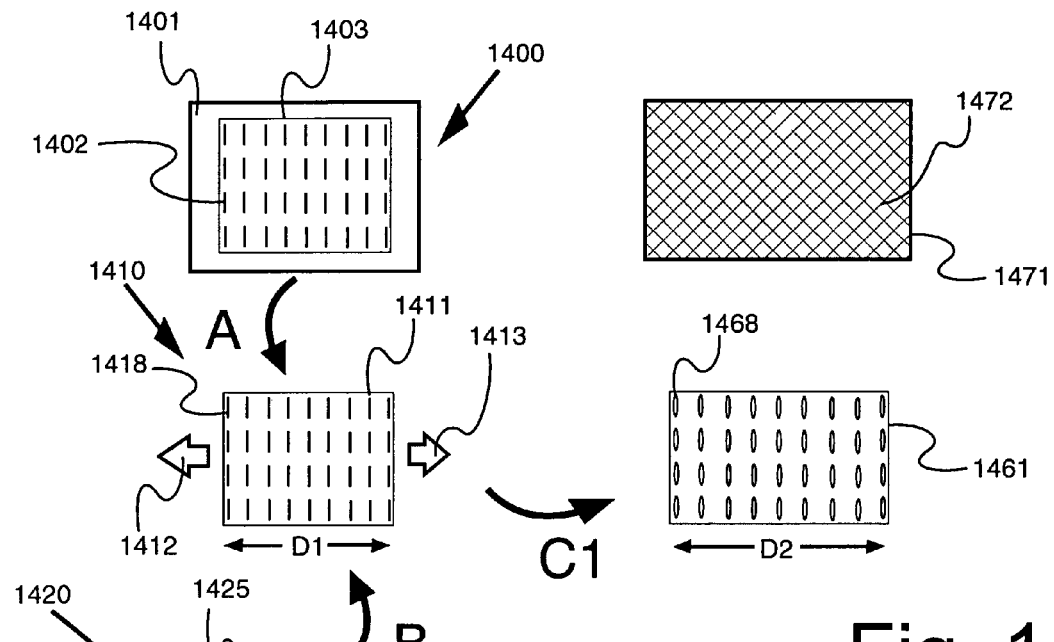
FIG. 14 illustrates alternate arrangement for skin treatment or for delivery of transdermal agent.
Figure 14:
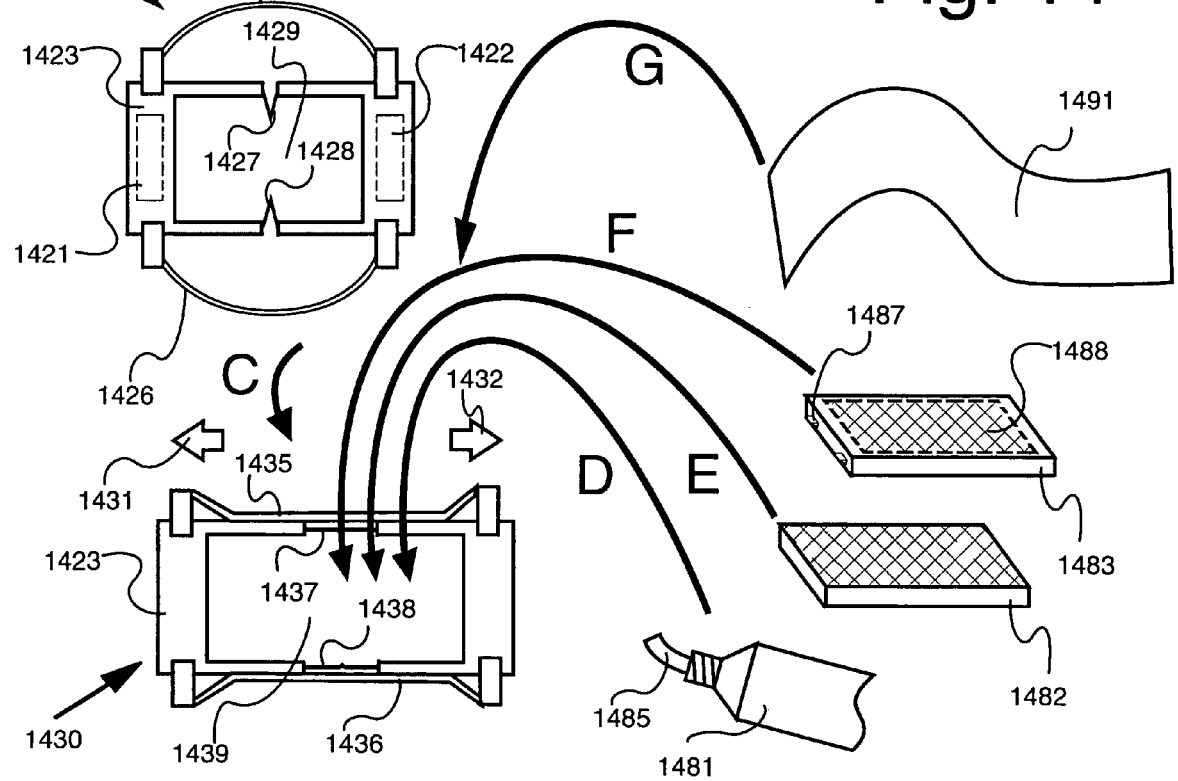

As compared with other skin stretching designs previously demonstrated in the prior art, such as the articles demonstrated in the US Patent application publication US 2002/10111600, it should be noted that the designs of the treatment arrangement assemblies of FIG. 4a, FIG. 9a, 1320 of FIGS. 13 and 1420 of FIG. 14 are especially suitable to be automatically manufactured in mass volume. The single piece frame 1423 provides both the functions of the attachment member as well as the distance maintenance means. The cost per unit is significantly lower and the ease of operation is significantly improved. In addition, when packaged products of different size, shape, extension ratio R, or different stretch force are required to meet the different needs of the user, the product designs making use of the principle of operations of the disclosed novel embodiments will be able to deliver significantly simple manufacturing tooling designs, lower manufacturing tooling investment, lower product cost and fast market response time as compared with the embodiments of the prior art.

From the foregoing, it should now be appreciated that applicant has disclosed herein embodiments of a complete low cost high efficiency skin treatment arrangement suitable for enhancing treatment result of deteriorated skin, such as wrinkle lines or scar of wounds, or for improving delivery of transdermal agents. Although detailed embodiments of the invention have been disclosed, it is recognized that variations and modifications, all within the spirit and principle of the invention, will occur to those skilled in the art. It is accordingly intended that all such variations and modifications be encompassed by the appended claims.

I claim:

1. A method for applying an agent to a surface of human skin; said method comprises the following steps (a) to (d):
   (a) providing a penetrating device having multiple miniature penetrating protrusions to create miniature penetrating openings to said surface of said human skin;
   (b) providing an arrangement having at least one attachment member having a position A and a position B separated at a distance D1 apart to define an initial mode;
   (c) said arrangement, further comprising attaching means configured for attaching said position A and position B to said surface of said human skin; and
   (d) said arrangement, further comprising at least one distance maintenance member or distance maintenance means structured for maintaining said position A and position B at a distance D2 apart to define a treatment mode; wherein D2 is longer than D1, and wherein said treatment mode is further arranged to broaden the miniature penetrating openings of said surface of said human skin in said treatment mode; wherein said method is further characterized by at least one of the following characteristics (1) to (6):
   (1) wherein said attachment member is configured to comprise a single piece component defined by at least one of the following characteristics:
      (i) wherein said position A, position B are portions of said single piece component; or
      (ii) said single piece component having a first end proximate to said position A and a second end proximate to said position B; and said first and second ends are fixedly connected to said distance maintenance member or said distance maintenance means;
   (2) wherein said distance maintenance member or said distance maintenance means is configured to comprise at least one flexible portion essential for extending said positions A and B and for maintaining said distance D2, wherein said distance maintenance member or said distance maintenance means is one single piece component;
   (3) wherein said attachment member comprises a flexible or elastic portion located in between said positions A and B; and wherein said flexible or elastic portion is configured for providing a pressure pushing said treatment agent towards the surface of said human skin, wherein said attachment member is one single piece component;
   (4) wherein said distance maintenance member or said distance maintenance means is irremovably attached to said attachment member, wherein said distance maintenance member or said distance maintenance means is one single piece component;
   (5) wherein said method further comprising a step of providing a treatment portion or a treatment member having an agent; and said treatment portion or said treatment member is irremovably connected to said attachment member, wherein said attachment member is one single piece component;
   (6) wherein said arrangement is a three layers structure, wherein said distance maintenance means defines a first layer, said attachment member defines a second layer, and said attaching means defines a third layer, and wherein said second layer is in between said first layer and said third layer.

2. The method of claim 1 wherein said attachment member, said attaching means and said distance maintaining means are constructed as a single piece assembly.

3. The method of claim 1 further comprising at least one of the following steps:
- (e) applying an agent to said surface of said human skin;
- (f) applying an agent on a treatment portion or treatment member located between said attachment member and said surface of said human skin;
- (g) providing a treatment portion or treatment member having a built-in agent;
- (h) applying an agent to said attachment member before said attachment member is applied to said surface of said human skin;
- (i) providing an agent container wherein said agent container contacting with said surface of said human skin;
- (j) providing a wrinkle relief agent or a scar relief agent to said surface of said human skin;
- (k) providing an absorbable agent in a solid form, wherein said absorbable agent making contact with said surface of sa human skin;
- (l) applying an agent to said surface of said human skin, and applying an adhesive bandage or tape on top of said attachment member, for securing said treatment mode.

4. The method of claim 1 further characterized by at least one of the following characteristics (7) to (13):
- (7) said attaching means is adhesive for adhering said attachment member to said surface of said human skin;
- (8) said attaching means is stitch for stitching said attachment member to said surface of said human skin;
- (9) said treatment portion or treatment member is fixedly connected to said attachment member;
- (10) said attachment member is dimensioned and shaped to fit a predefined type or shape of wrinkle line or wound of said surface of said human skin;
- (11) the maximum distance of D1 is 2 inches;
- (12) said treatment mode is achieved by squeezing or pushing at least a part of said distance maintenance member or said distance maintenance means;
- (13) said arrangement comprising a specific pre-determine extension ratio R, wherein R=D2/D1.

5. The method of claim 1 further comprising providing said arrangement and said penetrating device in a package.

6. The method of claim 1 further comprising at least one of the following characteristics (7) to (8):
- (7) providing a package comprising said attachment member, wherein said attachment member is a plurality attachment members of different shapes dimensioned for treating different locations of said human skin;
- (9) a package comprises said arrangement and said penetrating device, wherein said attachment member is a plurality attachment members of different stretch forces or different extension ratio R provided for treating different locations or different conditions of said human skin under treatment.

7. The method of claim 1 wherein said treatment portion or treatment member is configured for providing an agent.

8. The method of claim 1 wherein said attachment member and said distance maintaining means are constructed as a single piece component.

9. A method for applying an agent to a surface of human skin; said method comprises the following steps:
- (a) providing an arrangement having at least one attachment member having an elastic or flexible portion, said attachment member further comprises a position A and a position B separated at a distance D1 apart to define an initial mode;
- (b) said arrangement, further providing attaching means configured for attaching said position A and position B to said surface of said human skin;
- (c) said arrangement, further providing at least one distance maintenance means structured for maintaining said position A and position B at a distance D2 apart to define a treatment mode, wherein D2 is longer than D1; and
- (d) transforming said initial mode to said treatment mode by pressing or squeezing a flexible portion of said distance maintenance means.

10. The method of claim 9 further comprises at least one of the following steps:
- (e) providing a penetrating device having multiple miniature penetrating protrusions to create miniature penetrating openings to said surface of said human skin; wherein said miniature penetrating openings are widen when said initial mode is transformed into said treatment mode;
- (f) providing a treatment portion or a treatment member configured for receiving an agent; and said treatment portion or said treatment member is irremovably connected to said attachment member;
- (g) providing a treatment portion or a treatment member configured for receiving an agent; and wherein said arrangement is a three layers structure, wherein said distance maintenance means defines a first layer, said attachment member defines a second layer, and said treatment portion or said treatment member defines a third layer, and wherein said second layer is in between said first layer and said third layer;
- (h) applying an agent to said surface of human skin;
- (i) applying an agent on a treatment portion or a treatment member located between said attachment member and said surface of said human skin;
- (j) providing a treatment portion or a treatment member having a built-in agent;
- (k) applying an agent to said attachment member before said attachment member is applied to said surface of sa human skin;
- (l) providing an agent container, wherein said container having an agent to contact with said surface of said human skin;
- (m) providing a wrinkle relief agent or a scar relief agent;
- (n) providing an agent, wherein said agent is provided in a solid form, and wherein said solid agent is absorbed into said human skin when said solid form agent applied or contacted with said surface of said human skin;
- (o) applying an agent to said surface of said human skin and an adhesive bandage or tape on top of said attachment member after, for securing said treatment mode.

11. The method of claim 9 further comprises at least one of the following characteristics:
- (1) wherein said attachment member is:
  - (i) a single piece component wherein said position A, position B are portions of said single piece component; or
  - (ii) a single piece component having a first end proximate to said position A and a second end proximate to said position B; and said first and second ends are fixedly connected to said distance maintenance means;
- (2) wherein said distance maintenance means is configured to comprise at least one flexible portion essential for extending said positions A and B and for maintaining said distance D2;
- (3) wherein said attachment means comprises a flexible or elastic portion located in between said positions A and B; and wherein said flexible or elastic portion is configured for providing a pressure pushing said treatment agent towards said surface of said human skin;
(4) wherein said distance maintenance means is irremovably attached to said attachment means;
(5) wherein said attaching means is configured for adhering said attachment member to said surface of said human skin;
(6) wherein said attaching means is configured for stitching said attachment member to said surface of said human skin;
(7) wherein said attachment member is dimensioned and shaped to fit a predefined type or shape of wrinkle line or wound of said human skin;
(8) wherein the maximum distance of D1 is 2 inches.

12. The method of claim 9 further providing said arrangement in a package.

13. The method of claim 12 further comprising at least one of the following characteristics (1) to (3):
(1) said attachment member is a plurality attachment members of different shapes dimensioned for treating different locations of said human skin;
(2) said attachment member is a plurality attachment members of different stretch forces or different extension ratio R provided for treating different locations or different conditions of said human skin under treatment;
(3) said package further comprises a penetrating device having multiple miniature penetrating protrusions to create miniature penetrating openings to said surface of said human skin.

14. An arrangement for delivering an agent to a surface of human skin comprising:
at least one attachment member having a position A and a position B separated at a distance D1 apart to define an initial mode;
attaching means configured for attaching said position A and position B to said surface of said human skin;
at least one distance maintenance member or distance maintenance means structured for extending and maintaining said position A and position B at a distance D2 apart to define a treatment mode, wherein D2 is longer than D1;
wherein said attachment member is a single piece component having said position A at a first end, and position B at a second end; and said single piece component further comprises at least a first flexible region located between said position A and said position B.

15. The arrangement of claim 14 wherein said distance maintenance member or said distance maintenance means is part of the single piece component of said attachment member.

16. The arrangement of claim 14, said attachment member further comprising a second flexible region configured for said distance maintenance member or said distance maintenance means to transform from said initial mode into said treatment mode and to maintain said treatment mode.

17. The arrangement of claim 14 further comprising a hollow region in between said position A, said position B and said first and second flexible regions.

18. The arrangement of claim 17 further comprising an agent, wherein said hollow region is dimensioned to accept said agent, wherein said agent is provided in at least one of the following forms:
(a) ointment form;
(b) a solid form, wherein said agent is configured to absorb into said human skin when agent is contacting with said surface of said human skin;
(c) said agent is contained in a container, wherein said container is dimensioned to be accepted in said hollow region.

19. The arrangement of claim 14 further comprising a package having said arrangement of claim 14.

20. The arrangement of claim 19 further comprises at least one of the following:
(a) a penetrating device having multiple miniature penetrating protrusions configured to create miniature penetrating openings to said surface of said human skin;
(b) an agent;
(c) a disinfectant;
(d) an adhesive bandage or tape configured for maintaining and securing of said treatment mode.

* * * * *